US00PP18861P2

(12) United States Plant Patent
Zary

(10) Patent No.: US PP18,861 P2
(45) Date of Patent: Jun. 3, 2008

(54) SHRUB ROSE PLANT NAMED 'JACMORDE'

(50) Latin Name: *Rosa hybrida*
Varietal Denomination: JACmorde

(75) Inventor: Keith W. Zary, Agoura Hills, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 56 days.

(21) Appl. No.: 11/187,390

(22) Filed: Jul. 21, 2005

(51) Int. Cl.
*A01H 5/00* (2006.01)

(52) U.S. Cl. ..... Plt./107

(58) Field of Classification Search ..... Plt./107
See application file for complete search history.

(56) References Cited

PUBLICATIONS

GTITM UPOVROM Citation for 'JACMORBL' as per ZA PBR 03854; Jun. 15, 2003.*

* cited by examiner

*Primary Examiner*—Kent Bell
(74) *Attorney, Agent, or Firm*—Klarquist Sparkman LLP

(57) ABSTRACT

Shrub rose plant characterized by its deep pink blooms presented in clusters; ease of propagation by hardwood or softwood cuttings; compact, well-branched habit; resistance to common fungal diseases, and hardiness to Zone 4.

1 Drawing Sheet

Genus and species: *Rosa hybrida.*
Variety denomination: 'JACmorde'.

ORIGIN OF THE INVENTION

The present invention relates to a new and distinct variety of a shrub rose plant named 'JACmorde' which was originated by me by crossing the variety 'Morden Blush' (U.S. Plant Pat. No. 8,054), with an unnamed red floribunda seedling (not patented) ('JACient' (U.S. Plant Pat. No. 6725)×'KORholst' (U.S. Plant Pat. No. 6117)).

BACKGROUND OF THE INVENTION

The primary objective of this breeding was to produce a new rose variety having the compact habit, cold hardiness, disease resistance of the female parent combined with the large flower, glossy foliage and big flower clusters of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deep pink blooms presented in clusters.
2. Ease of propagation by hardwood or softwood cuttings.
3. Compact, well-branched habit.
4. Resistance to common fungal diseases.
5. Hardy to Zone 4.

Asexual reproduction of this new variety by cuttings, as performed at Wasco, Calif., shows that the foregoing and all other characteristics and distinctions come true to form and are established and transmitted through succeeding propagations.

Comparison With Parents

Compared to the female parent 'JACmorde' has larger flowers, dark versus light pink flower color and fewer petals. Compared to the male parent, 'JACmorde' has dark pink versus red blooms and greater resistance to blackspot and rust.

Comparison With Similar Variety

The closest variety to 'JACmorde' is 'PRObril' (Brilliant Pink Iceberg) (PP12,645). 'JACmorde' is more compact, has greater resistance to powdery mildew and black spot and has fewer petals.

Brief Description of the Illustration

The accompanying illustration shows typical specimens of the vegetative growth and flowers of this new variety in different stages of development, depicted in color as nearly true as it is reasonably possible to make the same in a color illustration of this character.

Detailed Botanical Description

The following is a detailed description of my new rose cultivar with color descriptions using terminology in accordance with the Royal Horticultural Society (London) Colour Chart© 2001, except where ordinary dictionary significance of color is indicated.

Parentage:
*Seed parent.*—'Morden Blush' (PP 8054).
*Pollen parent.*—Unnamed red floribunda seedling (not patented), ('JACient' (PP6725)×'KORholst' (PP6117)).

Observations made from January 2003 to September 2004 from plants commencing at three years of age grown in a garden environment at Somis, Calif.

FLOWER

Blooming habit: Continuous.

Bud:

*Size.*—About 30 mm long and 20 mm in diameter when the petals start to unfurl.

*Form.*—The bud form is long, pointed ovoid.

*Color.*—When sepals first divide, bud color is Red-Purple Group N57D. When half blown, the upper sides of the petals are Red-Purple Group N57C and the lower sides of the petals are Red-Purple Group N57D.

*Sepals.*—Color: Upper surface: Green Group 138C. Lower surface: Yellow-Green Group 146C. Length: 25–28 mm. Width: 8–10 mm. Shape: Acuminate. Surface texture: Hoary. There are three lightly to normally appendaged sepals. There are two unappendaged sepals with hairy and glandular edges.

*Receptacle.*—Color: Yellow-Green Group 146A, can be Greyed-Purple Group 183A in areas exposed to bright sun. Shape: Funnel. Size: Small, about 7–8 mm long×6–7 mm wide. Surface: Smooth.

*Peduncle.*—Length: Short, averaging about 50–55 mm. Surface: Glandular. Color: Yellow-Green Group 146C, can be Greyed-Purple Group 183A in areas exposed to bright sun. Strength: Stiff, erect.

Bloom:

*Size.*—Medium: Average open diameter is about 8–9 cm.

*Height.*—25–30 mm.

*Borne.*—Several together in pyramidal clusters of 3–7 blooms.

*Stems.*—Strength: Strong. Average length is about 40–50 cm with a diameter of 5–6 mm.

*Form.*—When first open: High centered. Permanence: Flattens.

*Petalage.*—Number of petals under normal conditions: 15.

*Color.*—The upper sides of the inner petals are Red-Purple Group N57C. The reverse sides of the inner petals are Red-Purple Group N57D. The base of each petal has a White Group 155A color spot, 5 mm×7 mm. The major color on the upper sides is Red-Purple Group N57C.

*Variegations.*—There are occasional White Group 155A streaks on the guard petals.

*Discoloration.*—The general tonality at the end of the first day: No change. At the end of the third day: No change. Further aging: By day 4 or 5, there is a general fading.

*Fragrance.*—Moderate, clove.

Petals:

*Texture.*—Thick, leathery.

*Shape.*—Obovate.

*Surface.*—Smooth.

*Margin.*—Entire. Apex Shape: Retuse. Base Shape: Rounded.

*Form.*—Flat.

*Arrangement.*—Imbricated.

*Petaloids.*—Number: 1 or 2. Color: Red-Purple Group N57C to Red-Purple Group N57D.

*Persistence.*—Petals drop off cleanly before drying.

*Lastingness.*—On the plant: Fair (about 5 days). As a cut flower: Fair (about 5–6 days).

Reproductive parts:

*Stamens.*—Number: 150. Length: 8 mm. Anthers: Length: 2 mm. Color: Orange-Yellow Group 22C. Arrangement: Regular around styles. Filaments: Color: Greyed-Purple Group 185D. Length: 6 mm. Pollen: Color: Orange Group 26C.

*Pistils.*—Number: 50–60. Length: 5 mm. Styles: Color: Greyed-Purple Group 183C. Length: 5 mm. Stigmas: Color: White Group N155A. Length: 1 mm.

*Hips.*—None observed.

PLANT

Form: Shrub.

Growth: Vigorous, upright, branching, compact.

Age at maturity: Two years.

Mature plant: Height: 100–110 cm. Width: 70–80 cm.

Rootstock: Own root.

Foliage: Number of leaflets on normal mid-stem leaves: 5 or 7.

*Size.*—Medium. About 130 mm long×90 mm wide.

*Quantity.*—Abundant.

*Color.*—New foliage: Upper side: Greyed-Purple Group 183A. Lower side: Greyed-Purple Group 183C. Old foliage: Upper side: Green Group 139A. Lower side: Green Group 139B.

Leaflets:

*Size.*—About 40 mm long×20 mm wide.

*Shape.*—Pointed oval.

*Base shape.*—Oblique.

*Apex shape.*—Acute.

*Texture.*—Leathery, glossy.

*Edge.*—Serrated.

*Serrations.*—Single.

*Petiole.*—Color: Yellow-Green Group 146C.

*Petiole rachis.*—Color: Yellow-Green Group 146C. Underside: Rough with prickles.

*Auricles.*—None.

*Stipules.*—Length: 12–13 mm; serrated.

*Disease resistance.*—Resistant to rust, powdery mildew and blackspot under normal growing conditions.

*Pest resistance.*—Not observed.

*Vein color.*—Yellow-Green Group 146B.

*Venation pattern.*—Reticulate.

Wood:

*New wood.*—Color: Greyed-Purple Group 183A. Bark: Smooth.

*Old wood.*—Color: Yellow-Green Group 146B. Bark: Smooth.

Prickles:

*Quantity.*—On main canes from base: 5–6 per 15 cm of stem. On laterals from main canes: 5–6 per 15 cm of stem.

*Form.*—Straight to hooked slightly downward.

*Length.*—8–10 mm.

*Color when young.*—Greyed-Purple Group 183B.

*Color when mature.*—Greyed-Orange Group 177B.

Small prickles:

*Quantity.*—On main stalks: None. On laterals: None.

Winter hardiness: Hardy to Zone 4.

I claim:

1. A new and distinct variety of rose plant of the shrub class, substantially as herein shown and described, characterized particularly by its deep pink blooms presented in clusters; ease of propagation by hardwood or softwood cuttings; compact, well-branched habit; resistance to common fungal diseases and hardy to Zone 4.

* * * * *

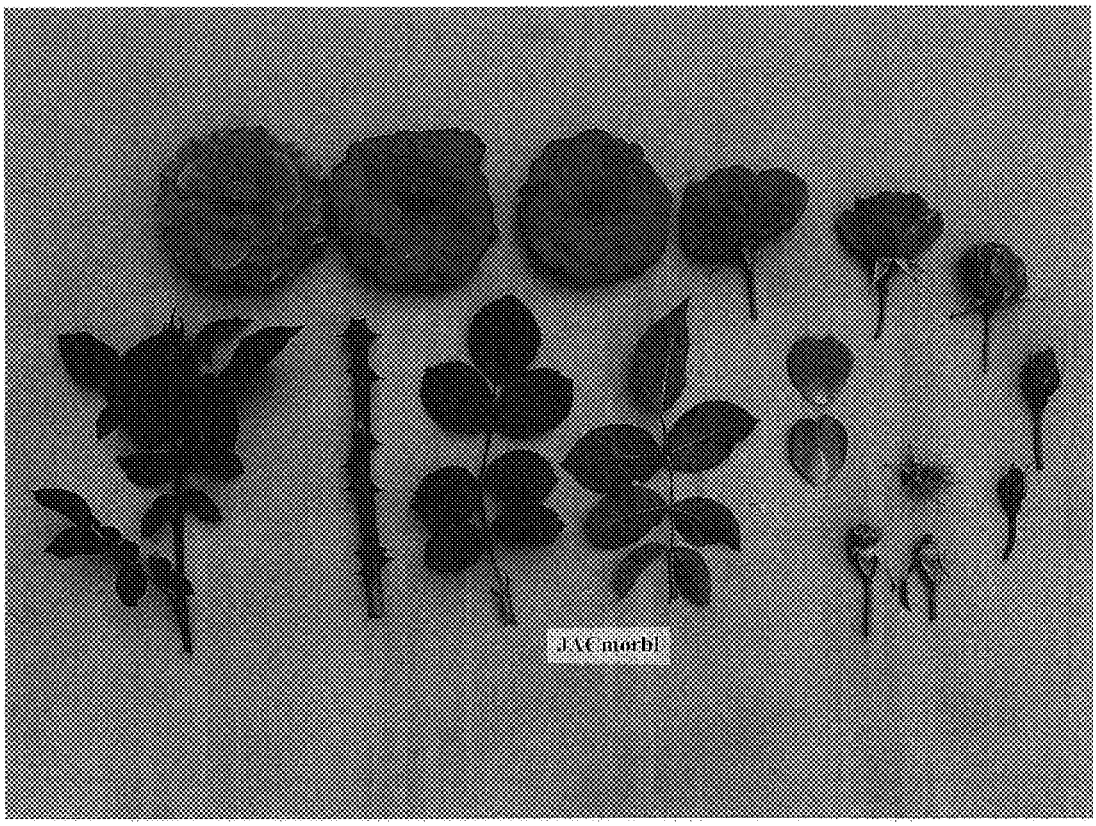
J.VC morbl